United States Patent
McCully (10) Patent No.: US 8,152,739 B1
(45) Date of Patent: Apr. 10, 2012

(54) ADJUSTABLE DUAL-BRUSH CERVICAL CYTOLOGY COLLECTION DEVICE

(75) Inventor: Christine Adrienne McCully, Camarillo, CA (US)

(73) Assignee: Christine A. McCully, Camarillo, CA (US)

( * ) Notice: Subject to any disclaimer, the term of this patent is extended or adjusted under 35 U.S.C. 154(b) by 706 days.

(21) Appl. No.: 12/284,178

(22) Filed: Sep. 19, 2008

Related U.S. Application Data (60) Provisional application No. 60/973,519, filed on Sep. 19, 2007.

(51) Int. Cl.
*A61B 10/00* (2006.01)

(52) U.S. Cl. .......................................... 600/569

(58) Field of Classification Search ........... 600/562–570
See application file for complete search history.

(56) References Cited

U.S. PATENT DOCUMENTS

| | | | |
|---|---|---|---|
| 2,955,591 A | 10/1960 | MacLean |
| 3,626,470 A | 12/1971 | Antonides et al. |
| 3,815,580 A | 6/1974 | Oster |
| 3,881,464 A | 5/1975 | Levene |
| 4,127,113 A | 11/1978 | Nollon |
| 4,700,713 A | 10/1987 | Kist |
| 4,754,764 A | 7/1988 | Bayne |
| 4,759,376 A | 7/1988 | Stormby |
| 4,762,133 A | 8/1988 | Bayne et al. |
| 4,873,992 A | 10/1989 | Bayne |
| 5,022,408 A | 6/1991 | Mohajer |
| 5,279,307 A | 1/1994 | Mohajer |
| 5,787,891 A | 8/1998 | Sak |
| 6,258,044 B1 | 7/2001 | Lonky et al. |
| 6,336,905 B1 | 1/2002 | Colaianni |
| 6,387,058 B1 | 5/2002 | Wallach |
| 6,521,190 B1 | 2/2003 | Edens et al. |
| 6,612,996 B2 | 9/2003 | Williams |
| 6,740,049 B2 | 5/2004 | Wallach |
| 7,413,551 B2 | 8/2008 | Decker et al. |

OTHER PUBLICATIONS

Bentz, The Unsatisfactory ThinPrep Test: Missed Opportunity for Disease Detection? Am J Clin Pathol 2002; 117:457-463. U.S.A.
Noel, Papanicolaou Smear Adequacy: The Effect of the Sampling Sequence. J Am Board Fam Pract 1993; 6:103-107. U.S.A. (Abstract Only).
Sullivan, Adenocarcinoma of the Cervix—The New Screening Opportunity. Trends in Cervical Health 2007;1. U.S.A.
Orr, The Efficacy and Safety of the Cytobrush During Pregnancy. Gynecol Oncol 1992; 44:260-262. U.S.A. (Abstract Only).
Hamblin, Papanicolaou Smear Adequacy: Effect of Different Techniques in Specific Fertility States. J Fam Pract 1985; 20:257-260. U.S.A.
Allington, Patient Characteristics and Endocervical Cell Recovery on Papanicolaou Smears. J Fam Pract 1985; 20:185-190. U.S.A.
Rome, Preclinical Cancer of the Cervix: Diagnostic Pitfalls. Gynecol Oncol 1985; 22:302-312. U.S.A. (Abstract Only).
Iftner, Chapter 12: Human Papillomavirus Testing with the Hybrid Capture 2 Assay. J Natl Cancer Inst Monogr 2003; 31:80-88. U.S.A.
Demay, Common Problems with Papanicolaou Smear Interpretation. Arch Pathol Lab Med 1997; 121:229-238. U.S.A. (Abstract Only).
Wilkinson, HPV Testing Update: The 2006 ASCCP Consensus Guidelines. Trends in Cervical Health 2007; 4:1-6. U.S.A.

*Primary Examiner* — Brian Szmal (57) ABSTRACT

A method and cytology device for manually adjusting the depth of endocervical sampling, and simultaneously sampling the endocervical canal and outer cervix using a dual-brush system. The device (38) comprises a primary cone-shaped endocervical sampling brush (40) adjacent to a secondary donut-shaped cervical sampling brush (42). The primary brush handle (52) is joined to the secondary brush handle (54) by means of a slidable rail (78), allowing adjustability of the primary brush length. The desired length and depth are visible by means of aligning incremental markings or measurements on the primary brush handle (80) with the positioning mark on the secondary brush handle (82). The brush handles are fixed in position and stabilized by means of a securing sheath (58), which has a pinch-release option to release or restore the friction existing between the sheath and the brush handles.

11 Claims, 6 Drawing Sheets

ADJUSTABLE DUAL-BRUSH CERVICAL CYTOLOGY COLLECTION DEVICE

CROSS-REFERENCE TO RELATED APPLICATIONS

This application claims the benefit of provisional patent application Ser. No. 60/973,519, filed 2007 Sep. 19 by the present inventor.

FEDERALLY SPONSORED RESEARCH

Not Applicable

SEQUENCE LISTING OR PROGRAM

Not Applicable

BACKGROUND

1. Field of Invention

This invention is directed to an improved method and apparatus for obtaining epithelial cell samples from the outer cervix and endocervix simultaneously, using an adjustable device with dual brushes for the collection and diagnosis of cancer and precancerous lesions.

2. Description of Prior Art

The collection and analysis of cellular samples for the detection of precancerous and cancerous lesions are vital steps in the prevention and treatment of cervical cancer.

The Pap smear has been one of the most simple, minimally invasive and inexpensive innovations in the history of women's health. Adequate sampling of cervical and endocervical cells are critical to accurate diagnosis. It is estimated that at least ⅓ of false-negative Pap smears are due to sampling issues.

A number of devices have been developed to collect samples from the cervix including cotton swabs, wooden and plastic spatulas, and cervical collection brushes with either fine nylon bristles or thick plastic bristles. Such devices are disclosed in U.S. patents to MacLean (U.S. Pat. No. 2,955,591), Antonides (U.S. Pat. No. 3,626,470), Oster (U.S. Pat. No. 3,815,580), Levene (U.S. Pat. No. 3,881,464), Nollon (U.S. Pat. No. 4,127,113), Kist (U.S. Pat. No. 4,700,713), Bayne (U.S. Pat. No. 4,754,764), Stormby (U.S. Pat. No. 4,759,376), Bayne et al. (U.S. Pat. No. 4,762,133), Bayne (U.S. Pat. No. 4,873,992), Mohajer (U.S. Pat. Nos. 5,022,408 and 5,279,307), Sak (U.S. Pat. No. 5,787,891), Lonky (U.S. Pat. No. 6,258,044), Colaianni (U.S. Pat. No. 6,336,905), Edens et al (U.S. Pat. No. 6,521,190), Williams (U.S. Pat. No. 6,612,996), Wallach (U.S. Pat. Nos. 6,387,058 and 6,740,049), and Decker et al. (U.S. Pat. No. 7,413,551). Currently the most effective method for adequate sampling is with a two step process using two instruments, the extended-tip spatula with an endocervical brush.

Nylon endocervical brushes have been proven to collect substantially more cells than original collection devices. They, however, cannot be adjusted in depth to allow for a patient's endocervical length or clinical history such as: stenosis occurring in postmenopausal women, pregnancy, prior cervical therapy, or prior inadequate endocervical sampling. Currently no brush devices contain means for identifying depth of endocervical sampling by displaying incremental markings or measurements.

Inadequate amounts of endocervical cells indicate that the transformation zone, the area that is the source of 90-95% of cervical cytologic atypia, has not been sampled. The location of the transformation zone varies in women, and, depending on factors such as age, genetics, and hormonal status, will migrate higher or lower within the endocervical canal. As a patient's age increases, the transformation zone will commonly be out of reach for the standard length endocervical brush. In a significant number of instances, when the specimens are not adequate because of lack of endocervical cells, the cell sample is less than optimal, and the patient is called for a re-examination. Repeat testing may unduly alarm the patient, and add unnecessary and unjustified medical expenses.

In pregnant patients, the location of the transformation zone may descend, but practitioners may be reluctant to sample deeply enough, or may choose to abandon the endocervical brush altogether. Although certain manufacturers have indicated endocervical brushes are not recommended in pregnant women (post 10-weeks) due to possible clinical complications, other studies have considered this concern to be unfounded. Studies have indicated that the nylon brush yields the highest rate of adequate smears throughout pregnancy, and showed no significant increased risk of serious outcomes with the use of the brush and the spatula. Although the endocervical brush produces more adequate Pap smears in pregnancy, there is currently no way to adjust for the depth of sampling in pregnant patients.

Another disadvantage to the endocervical brush is the lack of a stop or guide preventing the brush from entering too deeply into the endocervical canal. Inexperienced clinicians or medical students may insert the brush far beyond the transformation zone, and unknowingly sample the endometrium. Endometrial cells present on a Pap smear, other than during a menstrual cycle in pre-menopausal women, can have clinical significance to the clinician and patient by prompting an abnormal diagnosis.

Distinct endocervical sampling is also necessary as an increase in cervical adenocarcinoma has been noted, but for unknown reasons. Probable association with Human Papilloma Virus (HPV) types 16 and 18 is suggested. HPV types 16 and 18 account for 70% of all of cervical carcinomas. In the cervix, a typical aceto-white reaction is visibly observed by the clinician in affected areas, but glandular lesions are not visible, even during colposcopy.

Another disadvantage of the endocervical brush is that a large portion of the cell sample is lodged within the bristles of the brush, making it difficult to transfer all of the cells to the slide merely by wiping the bristles against the slide's smooth surface. Valuable diagnostic material is potentially lost, increasing the risk of a false-negative diagnosis. With the popularity of liquid-based cytology for monolayer preparations of cells, the accuracy of the resulting sample is again dependant on the successful and complete transfer of cell samples from the brush bristles to the container of fixative. Typically, the transfer is done by placing the bristled end of the cytology brush within the container holding the fixative solution. The brush is then manually rinsed within the solution in an attempt to dislodge the cells from the bristles. However, the rinsing action within the solution is often insufficient to dislodge or flush out all the cells that are contained on the bristles. On average, 37% of cellular material is lost when the collecting device is discarded, and the more intense the rinsing process, the less the loss of cells.

Another disadvantage is that cervical mucous tends to quickly air-dry unless immediately rinsed in the fixative solution, thickening and binding the cells to the bristles. Rinsing, or using a manual vortex action within the solution alone may not be adequate to release the cells from the bristles.

Some newer collection devices require the physical removal by handling and/or snapping off the brush or the device tip to avoid discarding it. This has a drawback in that a loss and disruption of cellular material by human manipulation occurs when attempting to remove the brush from the shaft. Another drawback is that the device tip typically this has to be removed at the laboratory prior to specimen processing. The shaft of the brush device can also interfere with the pipette tips of an automated pipettor, causing errors in sampling for assays utilizing automation such as molecular based tests for HPV, Chlamydia and Gonorrhea.

Other prior art cytology sampling tools designed to obtain a cellular sample from the cervix may combine both endocervical and outer cervix sampling regions into one device. These devices swab the surface of mucous-covered tissue by softly brushing the mucous layer of the endocervix and outer cervix at the same time. Such devices include brushes that have a contoured flat broom-like head with several rows of flexible plastic bristles arranged in a linear orientation. The center bristles are longer than the bristles on the ends, and the device is inserted into the endocervical canal until the lateral bristles bend against the outer cervix surface. The device is removed and the cells are swabbed across a glass slide, or, alternatively, the entire device is rinsed in a container of fixative solution for liquid-based cytology methods.

Several studies have indicated that a broom-like device with thicker collection bristles have a tendency to provide less than optimal sampling of the endocervix. Certain indications for one such broom-like device indicate rotation only in a clockwise direction. Each individual bristle has a flat and rounded side, and a counterclockwise rotation brings the rounded side in contact with the cervix instead of the flat side, reducing the device's effectiveness of collection.

Debate continues whether "all-in-one" broom-like devices appropriately sample the cervix. While agreement has been reached for sampling the transformation zone, differences in the estimated proximity of the transformation zone and the face of the outer cervix has led to doubt the effectiveness of sampling the endocervix and outer cervix with a broom-like device. It has been reported that broom-like devices appear to under-sample the endocervix, resulting in increased less than optimal Pap smear results based on lack of endocervical component. This may be due to the parallel positioning of the broom's bristles to the endocervical canal, or possibly the broom-like devices do not reach into the cervical opening as far as nylon endocervical brushes.

Another disadvantage of cervical broom-like devices is that although the bristles may be flexible, the clinician cannot manually adjust for different depth sampling of the endocervical canal.

A further disadvantage is that currently no broom-like devices contain means for identifying depth of endocervical sampling by displaying incremental markings or measurements.

Another disadvantage is that the base of the broom-like device is arranged in a linear configuration, requiring additional rotations of the device to sample the entire outer cervix area. Additional rotations of cytology collection devices cause unnecessary abrasion of the cervix surface, adding to patient discomfort and bleeding. Excessive red blood cells in a Pap smear can obscure the view of other diagnostic cells during the microscopic evaluation of the glass slide. A further disadvantage is that studies have indicated that excessive red blood cells introduced to the container of fixative solution may clog the filters of certain liquid-based cytology methods, blocking the epithelial cells from being deposited onto the glass slide.

Another disadvantage of the broom-like device occurs if a glass slide must be prepared instead of using a liquid-based cytology method. Liquid-based cytology methods require specific instruments, machinery, and personnel to process the specimen to the glass slide. This may be costly and prohibitive in parts of the world that are isolated, poor, or lack the benefit of technological advancements. When attempts are made to smear the cells collected from the broom-like device onto the glass slide, the linear base of the device prevents the clinician from rolling the device along the slide's surface. The device must be swept along the surface of the slide similar to a paint brush, and this may prevent the cells that are lodged between the plastic bristles from being transferred to the slide. If the clinician attempts to flatten and bend the plastic bristles onto the glass slide to release material, the endocervical components will be inadvertently mixed with the cervical components. Although it is not required for Pap smears, the definite separation of endocervical cells from cervical cells provides a visual advantage that aids in distinguishing the different cell types during microscopic evaluation.

Although the present cell collection brushes and broom-like devices are well-known and widely used, there continues to be many disadvantages associated with them. Existing brush systems have various drawbacks which may be addressed through the development and use of an improved endocervical and cervical cell sampler. Since it is important to obtain a large enough sample of cells to ensure the chances of detecting abnormal cells in a sample, it would therefore be highly desirable to have a method and device which increases the total number of endocervical and outer cervical cells collected from a patient. Further technological advancements in cytology such as molecular testing for Human Papilloma Virus, the virus responsible for all cervical carcinoma, will require even more cells to be collected in the future. As multiple testing is conducted from the same liquid-based collection container, a sample that is highly-enriched with cellular material would provide more opportunities for disease detection.

Other prior art sampling tools include an apparatus and method for obtaining a transepithelial specimen of a body surface using a non-lacerating technique, but the stiffness of its brush bristles lends itself for tissue sampling and is not appropriate for cytology.

Obvious advantages of this embodiment will become apparent from the detailed descriptions, taken in conjunction with the accompanying drawings.

SUMMARY

The device and method of the present invention have been designed to overcome the disadvantages of the prior art noted.

In accordance with the present embodiment, an adjustable cytology collection device with dual brushes designed to obtain cellular material from the endocervical canal and outer cervix simultaneously. The method includes providing a rotatable cervical cytology device having a primary cone-shaped endocervical cell collecting surface where the handle abuts another handle having a secondary donut-shaped cervical cell collecting surface. The cell collecting surfaces are sized and configured to be capable of scraping cytology cell samples from their respective areas when they are in contact with their respective regions and the device is rotated. The primary and secondary cytology brushes are also positioned with respect to each other so as to enable the endocervical canal and outer cervix to be sampled simultaneously as the device is rotated.

In one embodiment, the device of the present invention differs from prior devices for sampling endocervical cells in that it employs a unique design with ability to manually adjust to a specific endocervical sampling length, and is able to collect samples from the endocervix and outer cervix simultaneously. The device also includes predetermined measurements or incremental markings that will assist the clinician in choosing the desired endocervical sampling length.

In its broad form, the device includes a handle for manipulating and rotating the device, a primary cone-shaped cytology brush adjacent to the handle for collecting cells from the endocervical canal, and a secondary donut-shaped cytology brush adjacent to the handle for collecting cells from the outer cervix area.

In the preferred embodiment, the primary cone-shaped brush handle abuts the handle of the secondary donut-shaped brush and fits together by means of a rail. The handle of each brush comprises four surface areas; a flat interior edge where the rail is positioned, two flat adjacent edges opposite each other, and one exterior curved edge. On the interior flat edge of the primary brush is a protruding half-circle which fits into a similarly-shaped recessed area on the interior flat edge of the secondary brush, running along the length of the handle and forming a rail that the primary brush can slide along. The half-circle protrusion also serves as part of the wire housing of the primary endocervical brush, and the half-circle recess is adjacent to the wire housing of the secondary cervical brush.

In a preferred embodiment, the primary cone-shaped brush is adjusted to the desired length of endocervical sampling by sliding the handle along the rail to the appropriate position. Incremental markings or measurements are present on the primary handle, and a corresponding positioning marker is present on the secondary handle to help the clinician visualize a specific depth of endocervical sampling. This position can then be fixed by the use of a securing, clear plastic sheath positioned over the handles of both brushes.

The securing sheath is comprised of a hollow, transparent, semi-rigid and oval shaped plastic tube that locks the handles of the primary and secondary brushes together by applying pressure and friction against the curved edges of each brush handle. By manually exerting pressure on the sheath at the opposite flat edges of each brush, the semi-rigid oval sheath will bend into a more circular shape, and consequently release the pressure and friction that previously existed on the curved edge. With this "pinch-release" action, the primary brush can move freely along the rail of the secondary brush until the desired location is achieved. Releasing the pressure on the sheath will cause it to revert back into an oval shape, reinstating pressure and friction back onto the curved edges of each brush, and securing them both in place.

In a related embodiment, if it becomes necessary to separate the primary endocervical brush from the secondary cervical brush, pressure is exerted on the sheath and the primary brush is advanced slightly so that a significant gap appears between the primary brush head and the secondary brush head. The sheath is then slid upward and slightly through the center opening of the secondary donut-shaped brush. The clinician can then grasp the primary brush handle under the brush head, and slide the primary brush out through the sheath. Use of the sheath in this manner prevents the clinician from dislodging cellular material from the brushes upon separation, and contaminating the handle of the primary brush.

In a preferred embodiment, the cell samples will collect on the respective primary and secondary brushes after insertion and rotation of the device within the endocervical canal. The device is then withdrawn from the patient. The samples are removed from the device by: applying pressure to release the securing sheath, separating the primary and secondary brushes from each other, and smearing each brush on different areas of the same glass slide, or on two separate glass slides. In a related embodiment, the samples are removed from each brush by inserting the entire device into a container of fixative solution, applying pressure to release the securing sheath, then plunging the primary cone-shaped endocervical brush through the center opening of the secondary donut-shaped cervical brush several times. The bristles of each brush are soft enough not to cause cellular distortion when in contact with each other, and the plunging action exhibited will dislodge and release the cellular components into the fixative solution. A stop foot or barrier at the end of the secondary brush handle projects outward and prevents the primary endocervical brush from being pulled too far upward so that the rail is disengaged.

OBJECTS AND ADVANTAGES

It is a general object of the present invention to provide a device and method for Pap smear sampling which solves previous technical problems and overcomes the disadvantages of the prior art. A number of advantages of some embodiments of the present invention are:

(a) To provide an inexpensive cytology sampling device that can be used with or without the benefit of newer and costly technological advancements.

(b) To provide an inexpensive cytology sampling device that is disposable, efficient, and easy to maneuver.

(c) To provide a manually adjustable cytology sampling device that allows for varying depths of endocervical sampling.

(d) To provide a manually adjustable cytology sampling device where the endocervical depth can be fixed in place by the use of a securing sheath.

(e) To provide a manually adjustable cytology sampling device with two conjoined handles that are fixed, and rotate together by means of a securing sheath applied to both handles.

(f) To provide a manually adjustable cytology sampling device with added incremental markings or measurements to display the selected depth of endocervical sampling.

(g) To provide a dual-brush cytology device to collect cells from the endocervical canal and the outer cervix simultaneously.

(h) To provide a dual-brush cytology device that contains a primary cone-shaped endocervical brush and a secondary donut-shaped cervical brush, increasing the surface area of collecting bristles and producing a highly-enriched cell sample.

(i) To provide a dual-brush cytology device with an increased surface area of collection bristles to reduce the amount of rotations needed to adequately collect a sample.

(j) To provide a dual-brush cytology device in which fewer rotations are required while within the collecting area, reducing the amount of abrasion to the cell surfaces and minimizing patient discomfort and bleeding.

(k) To provide a dual-brush cytology device that reduces unnecessary abrasion and bleeding, eliminating obscuring blood on glass slides and the possibility of clogging the filters of certain liquid-based cytology methods, of which may prevent cells from being deposited on the slide.

(l) To provide a secondary donut-shaped cervical brush to act as a stop or guide when it contacts the face of the cervix, preventing the endocervical brush from entering too far into the endocervical canal and inadvertently sampling the endometrium.

(m) To provide a dual-brush cytology device where the primary cone-shaped endocervical brush can be plunged repeatedly through the opening of the secondary donut-shaped cervical brush while the device is submerged in a container of fixative solution, dislodging and releasing the cells from both brushes and resulting in a highly-enriched cell sample.

(n) To provide a dual-brush cytology device in which the primary endocervical brush can be separated from the secondary cervical brush and separate glass slides made for each, or, alternatively, each brush is applied to separate liquid-based cytology containers to allow for multiple molecular testing options.

(o) To provide a protective sheath for the primary brush handle to slide through when separating the brushes, eliminating the opportunity either to dislodge cells from the bristles, or contaminate the primary brush handle.

Advantages will become apparent from a consideration of the ensuing description and drawings.

BRIEF DESCRIPTION OF THE DRAWINGS

The following detailed description may best be understood by reference to the following drawings in which.

DRAWINGS

Reference Numerals 10 conventional wooden spatula
12 handle
14 long lobe
16 short lobe
18 endocervical brush
20 handle
22 cylindrical brush head with soft bristles
24 broom-like cytology device
26 handle
28 carrier
29 detachable head
30 thick plastic bristles
32 spiral biopsy brush
34 handle
36 stiff bristles
38 adjustable dual-brush cervical cytology collection device
40 primary cone-shaped endocervical brush with soft bristles
42 secondary donut-shaped cervical brush with soft bristles
44 primary brush wire
46 secondary brush wire
48 primary wire housing
50 secondary wire housing
52 primary brush handle
54 secondary brush handle
56 secondary foot stop
58 oval securing sheath (fixed/slidable/securing position)
62 flat exterior edge of primary handle
63 flat exterior edge of secondary handle
64 curved exterior edge of primary handle
65 curved exterior edge of secondary handle
66 primary wire
68 secondary wire
70 primary wire housing
72 secondary wire housing
74 primary half-circle protrusion
76 secondary half-circle recess 78 rail
80 primary handle incremental markings or measurements
82 secondary handle positioning mark
84 uterus
86 vagina
88 endocervical canal
90 outer cervix
92 transformation zone
94 liquid-based container of fixative solution
95 glass side
96 predominately endocervical material
97 predominately cervical material
98 solution with few cells
100 solution with moderate cells
102 solution heavily-enriched with cells

DETAILED DESCRIPTION OF THE PREFERRED EMBODIMENT AND OPERATION

Figure 1A:
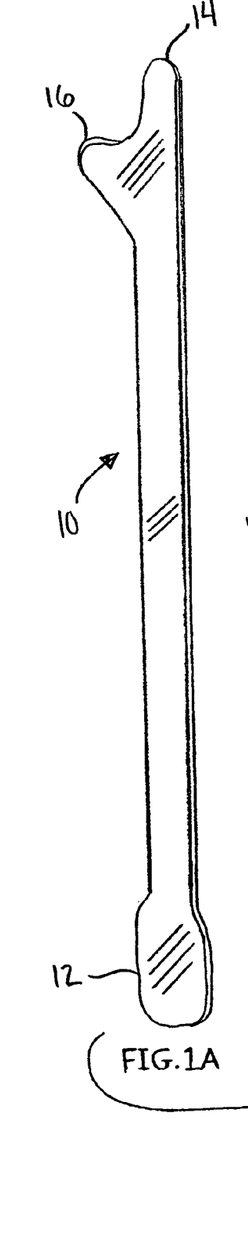
FIG. 1A of sheet 1 is a perspective view of a conventional prior art wooden spatula.

FIG. 1A illustrates a conventional wooden spatula 10, a device for sampling the transformation zone, the outer cervix, and to a lesser degree, the endocervix. As shown in FIG. 1A, one end of the spatula 10 is provided with a handle portion 12 for manipulating the spatula. At its other end, spatula 10 is provided with a long lobe 14 and a short lobe 16. In order to collect cervical cell samples, the spatula 10 is inserted into the vagina and long lobe 14 is inserted into the endocervical canal entrance until the short lobe 16 comes into contact with the face of the outer cervix. The device is rotated using the handle 12, and cells are scraped off onto the wooden spatula. The spatula 10 is then withdrawn from the patient and the cellular material is smeared onto a glass slide for microscopic evaluation. Very few cells from the endocervix are collected as the spatula's short lobe 16 merely pivots about the endocervical canal entrance.

Figures 1B, 1C:
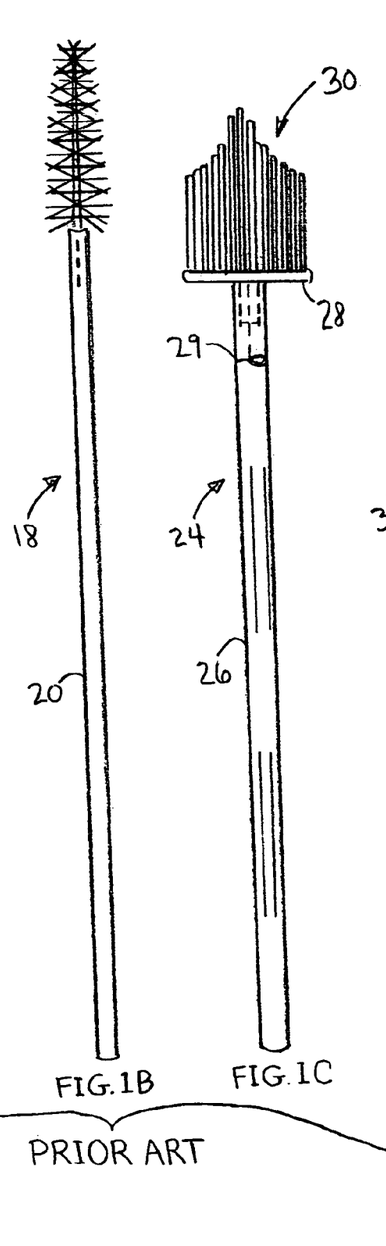
FIG. 1B of sheet 1 is a perspective view of a prior art endocervical brush.
FIG. 1C of sheet 1 is a plan view of a prior art broom-like cytology collection device.

FIG. 1B illustrates an endocervical brush 18, which is one of the more commonly used devices for endocervical sampling. Brush 18 has a thin cylindrical stem-like handle 20 which is between 5½" to 7½" long. One end of handle 20 is provided with a generally cylindrical brush portion with soft bristles 22, which is generally about ¾" long and about ¼" in diameter. Endocervical samples are taken by inserting the brush into the endocervical canal until the clinician deems it the appropriate depth, and then slowly rotating it one-half to one full turn. The brush is then removed from the endocervical canal and a Pap smear is prepared by rolling and twisting the brush on the glass slide. Because of the cylindrical shape of the endocervical brush 18, it is difficult to sample the outer area of the cervix.

FIG. 1C illustrates a broom-like cytology collection device 24 with thick, plastic bristles 30 connected to a carrier 28. The device 24 is inserted into the endocervical canal until the shorter, outer bristles bend against the outer cervix and the longer, inner bristles are within the endocervix. The device is rotated using the handle 26 and cells from the endocervix and outer cervix are collected, then the head of the device 24 is smeared onto a glass slide like a paint brush, or rinsed in a container of liquid-based cytology fixative solution. Some such devices have a detachable head 29 that can be snapped off and left in the container of fixative solution. Studies have suggested that the broom-like collection device 24 has a tendency to provide suboptimal sampling of the endocervix, possibly due to the parallel positioning of the bristles 30 to the endocervical canal.

Figure 1D:
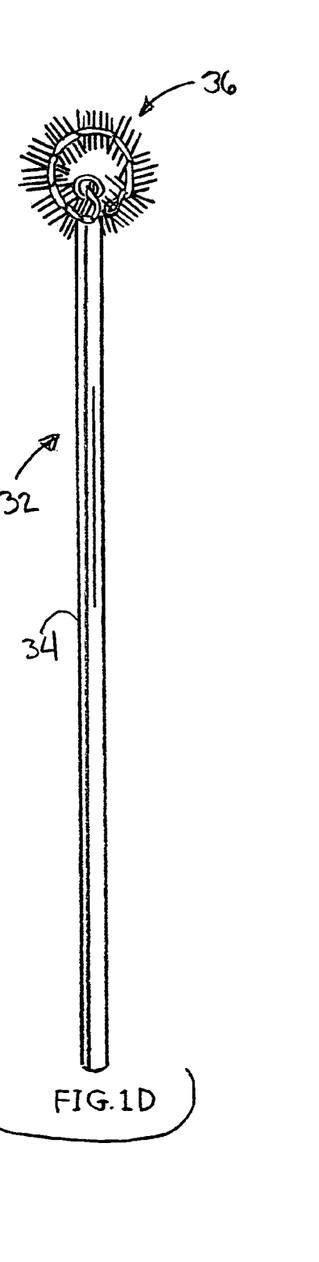
FIG. 1D of sheet 1 is a perspective view of a prior art apparatus for obtaining transepithelial specimens of a body surface using a non-lacerating technique, otherwise resembling a spiral-shaped biopsy instrument.

FIG. 1D illustrates a spiral-shaped device 32 not used for cytology, but for obtaining tissue biopsies of the outer cervix instead. The device is inserted into the vagina and positioned against the cervix, rotated with handle 34 while applying moderate pressure, causing the extremely stiff bristles 36 to abrade the surface so that deeper epithelial tissue samples are obtained. The stiffness of the device's bristles 36 render it unusable for Pap smear cytology.

Figures 2A, 2B, 2C, 2D:
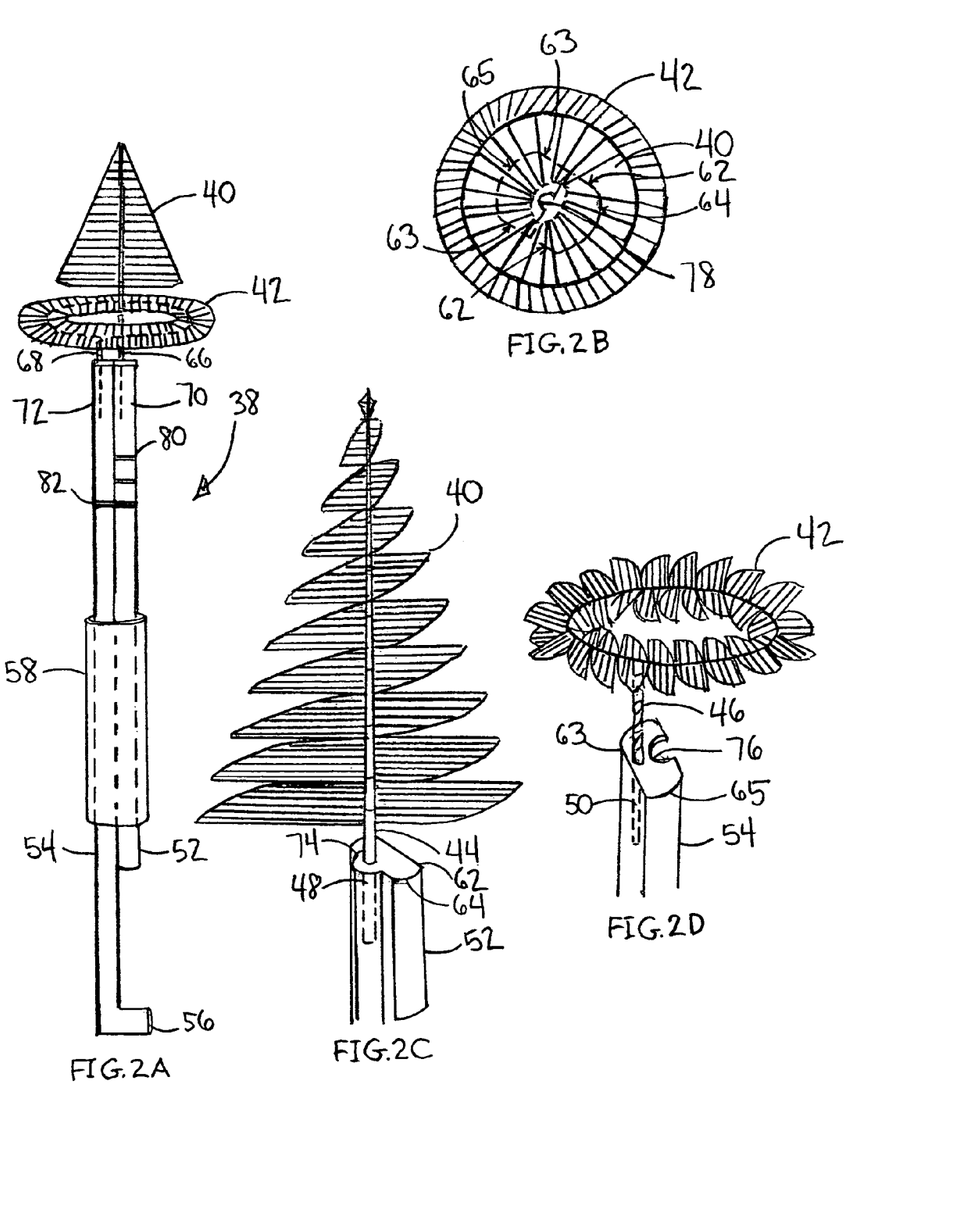
FIG. 2A of sheet 2 is a front perspective view of the preferred embodiment of the present invention for dual-sampling the endocervix and outer cervix simultaneously.
FIG. 2B of sheet 2 is an enlarged, top plan view of the primary cone-shaped endocervical brush and the secondary donut-shaped cervical brush.
FIG. 2C of sheet 2 is an enlarged, perspective view of the primary cone-shaped endocervical brush.
FIG. 2D of sheet 2 is an enlarged, perspective view of the secondary donut-shaped cervical brush.

Referring to the drawings, and in particular FIGS. 2A and 2B, there is depicted an endocervical and outer cervical sampling device 38, constructed in accordance with the preferred embodiment.

Figure 3:
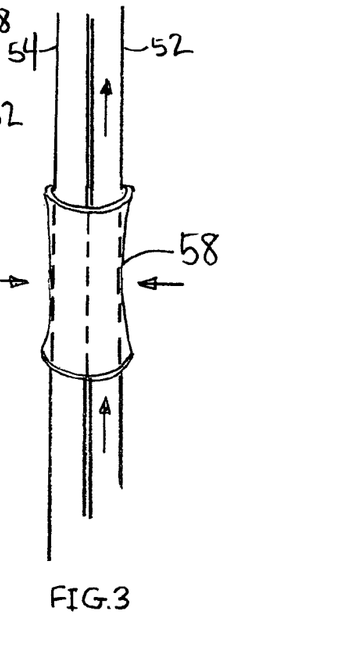
FIG. 3A of sheet 3 is a perspective view of the securing sheath surrounding the primary and secondary brush handles. The purpose is to illustrate the brush handles in a fixed position.
FIG. 3B of sheet 3 is a detailed cross-section of the primary and secondary brush handles, joined together by a half-circle protrusion resting within a half-circle recessed area respectively, forming a rail.
FIG. 3C of sheet 3 is a perspective view of the securing sheath with manual pressure being exerted on the exterior flat edges of the brush handles.
FIG. 3D of sheet 3 is a demonstration of exerting manual pressure on the securing sheath. The purpose is to illustrate the release of friction and pressure on the brush handles, allowing movement.
Figure 3A:
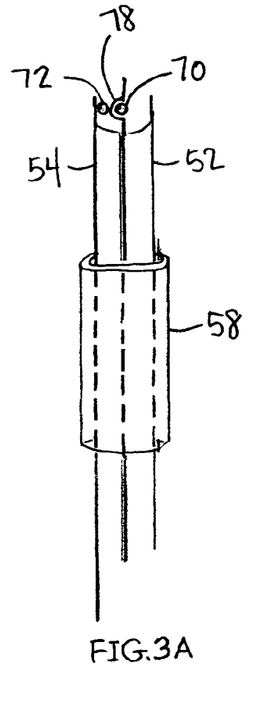
Figure 3B:
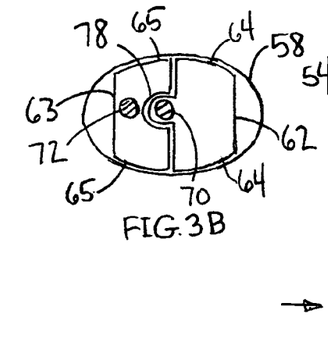
Figure 3D:
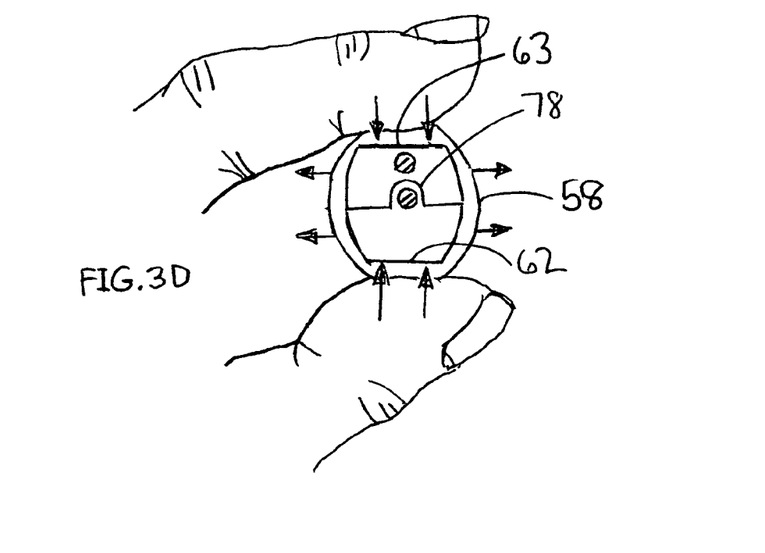

The cytology sampling device 38 comprises a primary cone-shaped endocervical brush with soft bristles 40 shown in (FIG. 2C), and a secondary donut-shaped cervical brush with soft bristles 42 shown in FIG. 2D. The handle 52 of the primary endocervical brush 40 and the handle 54 of the secondary cervical brush 42 are fixed in place by means of a securing sheath 58 (FIG. 3A). Both handles are interlocked but movable along the means of a sliding rail 78, shown in FIG. 3B. The rail 78 comprises a half-circle protrusion 74 from its primary brush handle 52 at the interior flat edge, and is fitted into a half-circle recess 76 located on the interior flat edge of the secondary brush handle 54. The protrusion 74 also comprises the primary wire housing 70 that provides a base for the primary wire 66, which supports the primary endocervical brush 40. The recess 76 is adjacent to the secondary wire housing 72, providing a base for the secondary wire 68, which supports the secondary cervical brush 42.

Referring to FIGS. 3A, 3B, 3C, and 3D, the cytology sampling device 38 can be adjusted to varying endocervical depths by exerting pressure on the oval securing sheath 58 at the flat exterior edges 62 of the primary handle 52, and flat exterior edges 63 of the secondary handle 54 simultaneously. This in turn bends the oval sheath 58 into a circular shape and releases the pressure and friction on the curved exterior edge 64 of the primary handle, and the curved exterior edge 65 of the secondary handle. The primary brush handle 52 can then be slid along the length of the secondary brush handle 54, adjusting the distance between the primary brush 40 and the secondary brush 42.

As shown in FIG. 2A, there are incremental markings or measurements 80 on the primary brush handle 52 that aligns with a single positioning mark 82 on the secondary brush handle 54. This feature allows the clinician to select an endocervical sampling depth prior to the device being inserted into the vagina. The desired position is held in place by the securing sheath 58.

Figures 4A, 4B, 4C:
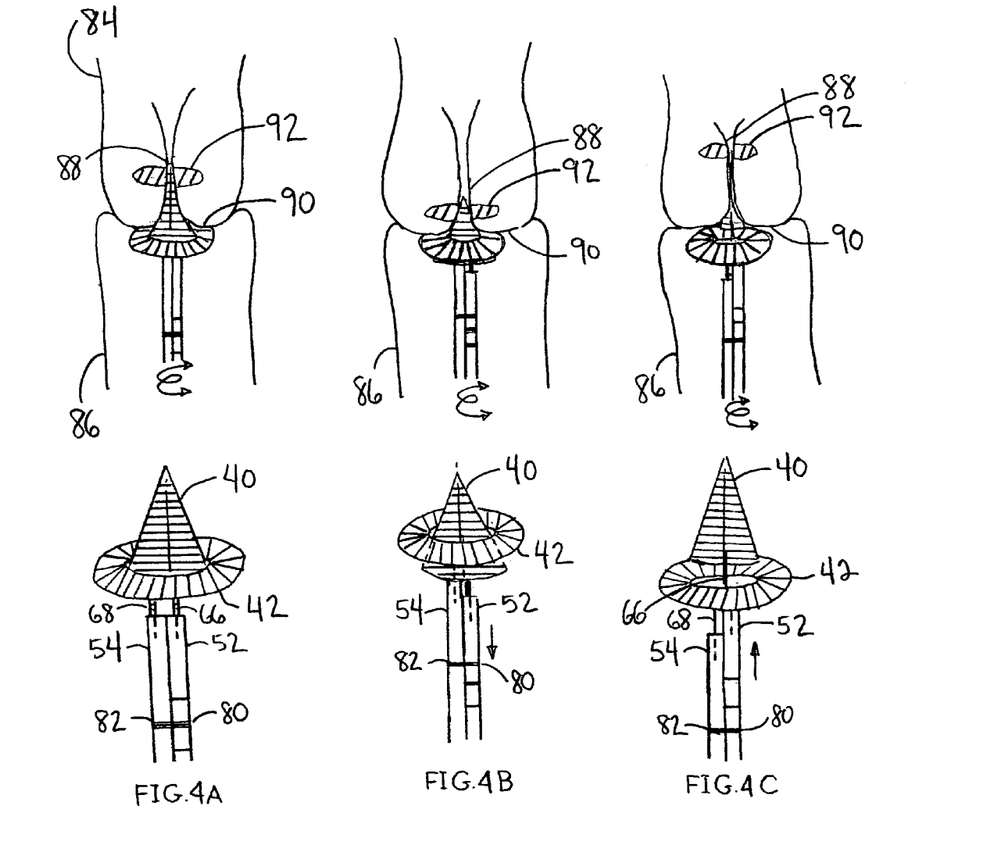
FIG. 4A of sheet 4 shows the device in the present method of use adjusted to a moderate enodocervical sampling depth.
FIG. 4B of sheet 4 shows the device in the present method of use adjusted to a shallow endocervical sampling depth.
FIG. 4C of sheet 4 shows the device in the present method of use adjusted to a deeper endocervical sampling depth.

FIGS. 4A, 4B, and 4C show a series of illustrations demonstrating the use of the collecting device 38 after insertion into the vagina 86 and the uterus 84. The endocervical sampling depth is chosen by aligning the incremental markings or measurements 80 on the primary brush handle 52 with the positioning mark 82 on the secondary brush handle 54. Depending on the position of the transformation zone 92, the device can be adjusted to a shallow, moderate, or deeper sampling depth. The device 38 is inserted into the endocervical canal 88 until the secondary brush 42 comes in contact with the outer cervix 90, and the device is rotated one-half to one full turn to collect cellular material from the endocervix and outer cervix simultaneously. The device is withdrawn from the patient and several different methods of transferring material are available.

Figure 5A:
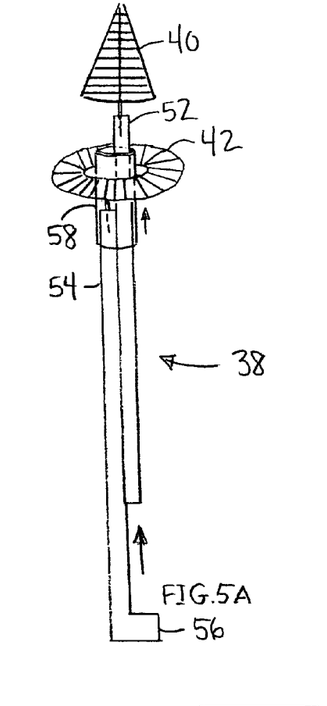
FIG. 5A of sheet 5 shows a perspective view of the securing sheath forming a protective shaft for the primary brush handle to slide through upon separation of the primary brush from secondary brush.
Figures 5B, 5C:
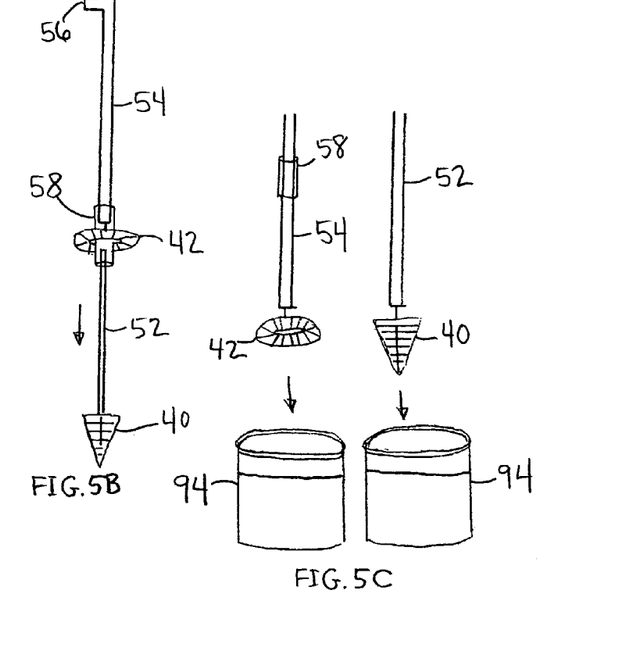
FIG. 5B of sheet 5 shows a perspective view of the separation of the primary endocervical brush from the secondary cervical brush.
FIG. 5C of sheet 5 shows a perspective view of the separated primary endocervical brush and the secondary cervical brush entering separate containers of fixative solution for liquid-based cytology methods.

After the cellular samples are collected, the primary brush 40 can be separated from the secondary brush 42 by first releasing the securing sheath 58 and sliding the sheath upward and slightly through the opening of the secondary cervical brush 42, as shown in FIG. 5A. This provides a protective shaft 58 from the same securing sheath 58 to allow an opening for the primary brush handle to slide through, and prevent the dislodging of cells and contamination of the handle. The clinician then grasps the primary brush handle 52 at a position above the secondary brush, and slides it through the center of the secondary brush 42, as shown in FIG. 5B. After separation, the primary brush 40 and the secondary brush 42 can be inserted into separate containers of fixative solution 94 (FIG. 5C), rinsed, and processed for microscopic evaluation or further molecular testing.

Figure 5D:
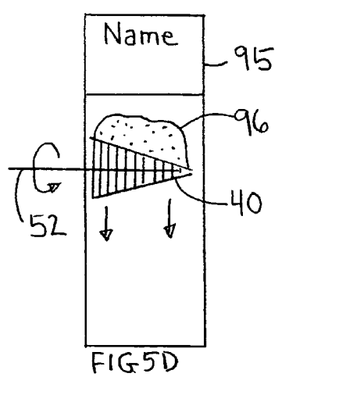
FIG. 5D of sheet 5 shows a schematic view of a method of transferring collected endocervical material from the primary brush to the glass slide.
Figure 5E:
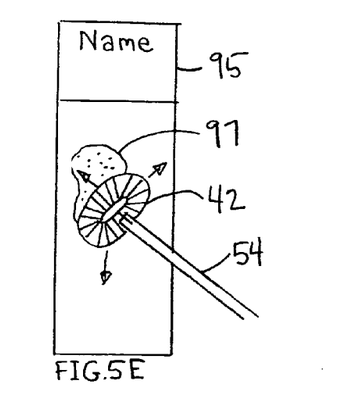
FIG. 5E of sheet 5 shows a schematic view of a method of transferring collected cervical material from the secondary brush to the glass slide.

FIGS. 5D and 5E show an alternative method of transferring cells from the brushes onto a glass slide 96. Primary brush 40 pressed on the slide and rolled or twisted by rotating the handle 52 to transfer cellular material. The secondary brush 42 is pressed and twisted against the glass slide 96 by rotating the handle 54 back and forth repeatedly along the length of the slide.

As shown in FIGS. 6A, 6B, 6C, and 6D, the device 38 utilizes a method for dislodging cells from the bristles of both brushes, and releasing them into a container of fixative solution 94.

Figure 6A:
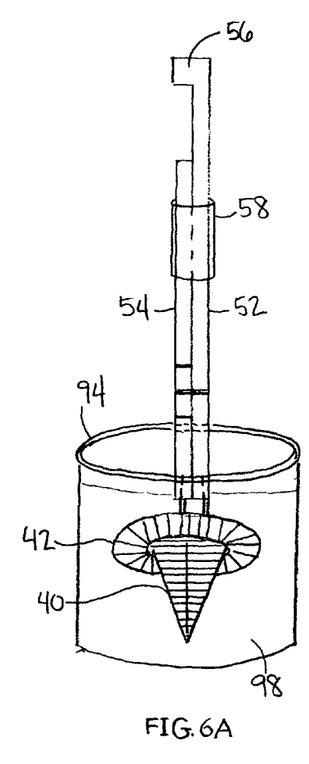
FIGS. 6A, 6B, and 6C of sheet 6 shows a series of schematic views of a method for dislodging cellular material from the brush bristles by mean of a plunging action, releasing an increasing number of cells into the container of fixative solution.

In FIG. 6A, the collection device 38 has been inserted into the container of fixative solution 94. Few cells have been dislodged from the bristles into container 98.

Figure 6B:
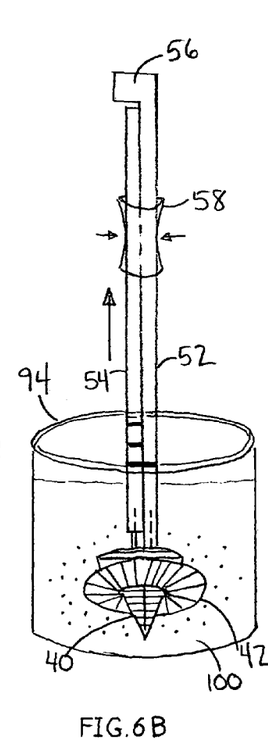

In FIG. 6B, with the collection device 38 still immersed in the container of solution, the primary brush handle 52 is pulled upward and slides along the length of the secondary brush handle 54 until it comes into contact with the secondary foot stop 56. The foot stop 56 acts as a barrier preventing the primary brush from sliding too far and disengaging the rail 78. The primary brush handle 52 is then pushed downward into the container of solution. By allowing the bristles of the cone-shaped primary brush 40 to come into contact with the bristles of the donut-shaped secondary brush 42, the cells contained on each are dislodged and released into the fixative solution. This step is repeated several times. A moderate amount of cells have been released into container 100.

Figure 6C:
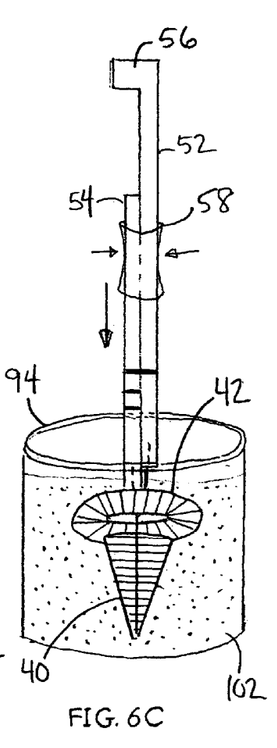

In FIG. 6C, after plunging the primary brush 40 through the opening of the secondary brush 42 several times, the resulting cellular yield in container 102 should be dramatically increased and produce a liquid-based cytology specimen highly-enriched with cells.

CONCLUSION, RAMIFICATIONS, AND SCOPE

The cytology collection device and method of the present embodiment is preferred over the prior art for a number of reasons. Specifically, the preferred embodiment's unique combination has the advantage of having:

dual-sampling brushes comprised of a primary cone-shaped endocervical brush and donut-shaped cervical brush for simultaneous collection of cells from the endocervix and the outer cervix;

an increased surface area of brush region allowing for an increase in the number of cells collected;

an adjustable endocervical sampling depth combined with incremental markings or measurements visible to the clinician;

a securing sheath to fix the endocervical depth position in place and stabilize the device;

a method for the pinch-release of the securing sheath to allow the primary brush handle to slide along the length of the secondary brush handle;

a rail designed to join the interior surface of both brush handles while still allowing movement;

a method to separate the primary endocervical brush from the secondary cervical brush if necessary;

a method for adjusting and choosing the desired depth of endocervical sampling;

a method to dislodge and release cells trapped within the bristles of the primary and secondary brushes, producing a highly-enriched cell sample for liquid-based cytology methods; and, an easy-to-use, inexpensive cytology collection device that can be used with conventional glass slides or liquid-based cytology methods.

Although the description above contains many specificities, these should not be construed as limiting the scope of the embodiments but as merely proving illustrations of some of the presently preferred embodiments.

Thus the scope of the embodiments should be determined by the appended claims and their legal equivalents, rather than by the examples given.

I claim:

1. An adjustable cervical cytology device for simultaneously collecting cell samples from the endocervix and outer cervix using a dual-brush device, said device comprising:

a primary handle comprising a proximal end, a distal end, and an exterior surface extending between the proximal and distal end, and a cone-shaped, soft-bristled endocervical brush located at the distal end of said primary handle;

a secondary handle comprising a proximal end, a distal end, and an exterior surface extending between the proximal and distal end, and a donut-shaped, soft-bristled cervical brush located at the distal end of said secondary handle;

a rail consisting of a half-circle protrusion on an interior flat edge of said primary handle fitted within a half-circle recess on an interior flat edge of said secondary handle;

a primary wire housing within said half-circle protrusion on said primary handle, said primary wire housing contains a semi-rigid braided wire wherein said wire supports said primary brush;

a secondary wire housing adjacent to said half-circle recess in said secondary handle, said secondary wire housing contains a semi-rigid braided wire wherein said wire supports said secondary brush an oval, semi-rigid plastic sheath positioned around said primary and secondary handles;

a foot stop positioned on the proximal end of said secondary handle;

incremental markings or measurements on the exterior surface of said primary handle; and a positioning mark on the exterior surface of said secondary handle.

2. The device of claim 1, wherein said primary and secondary handles are comprised of a rigid material.

3. The device of claim 1, wherein said primary or secondary brushes are comprised of fine, soft nylon.

4. The device of claim 1, wherein said sheath is comprised of a clear, semi-rigid material.

5. The device of claim 1, wherein said foot stop is a projection or barrier extending from the proximal end of said secondary handle.

6. The device of claim 1, wherein incremental markings or measurements are on the exterior surface of said primary and secondary handle.

7. A method of adjusting a depth of endocervical sampling on a device, said method comprising:

releasing a securing friction of a sheath by exerting pressure on flat, exterior edges on opposite primary and secondary handles, causing said sheath to bend away from opposite exterior curved edges on said primary and secondary handles;

holding said secondary handle stationary while sliding said primary handle along a rail until a desired endocervical sampling depth is selected by aligning incremental markings or measurements on an exterior of said primary handle with a positioning mark on said secondary handle; and releasing pressure on said sheath, thereby restoring said securing friction and fixing said desired endocervical sampling depth in place.

8. A method of collecting cell samples simultaneously from the endocervical canal and outer cervical area of a patient with a dual-brush sampling device, said method comprising:

releasing a securing friction of a sheath by exerting pressure on flat, exterior edges on opposite primary and secondary handles, causing said sheath to bend away from opposite exterior curved edges on said primary and secondary handles;

holding said secondary handle stationary while sliding said primary handle along a rail until a desired endocervical sampling depth is selected by aligning incremental markings or measurements on an exterior of said primary handle with a positioning mark on said secondary handle; and, releasing pressure on said sheath, thereby restoring said securing friction and fixing said desired endocervical sampling depth in place;

inserting a primary brush into the endocervical canal until a secondary brush contacts the surface of outer cervix;

slowly rotating said device clockwise and/or counterclockwise; and withdrawing said device from said patient.

9. A method of separating a primary brush from a secondary brush after collection of cellular material, the method comprising:

releasing a securing friction of a sheath by exerting pressure on flat, exterior edges on opposite primary and secondary handles, causing said sheath to bend away from opposite exterior curved edges on said primary and secondary handles;

holding said secondary handle stationary while sliding said primary handle upward along an interior rail;

grasping and pulling said handle of said primary brush upward and through said opening of said secondary brush, until said primary and secondary brushes are separated; and transferring cells from said primary and secondary brushes onto glass slides by rolling and twisting said primary and secondary brushes against a surface of said slides.

10. A method of separating a primary brush from a secondary brush after collection of cellular material, the method comprising:

releasing a securing friction of a sheath by exerting pressure on flat, exterior edges on opposite primary and secondary handles, causing said sheath to bend away from opposite exterior curved edges on said primary and secondary handles;

holding said secondary handle stationary while sliding said primary handle upward along an interior rail;

grasping and pulling said handle of said primary brush upward and through said opening of said secondary brush, until said primary and secondary brushes are separated; and transferring cells from said primary and secondary brushes into separate containers of fixative solution for liquid-based cytology analysis.

11. A method of dislodging and releasing cellular material collected on a primary and secondary brush, said method comprising:

inserting said primary and secondary brushes into container of fixative solution;

releasing a securing friction of a sheath by exerting pressure on flat, exterior edges on opposite primary and secondary handles, causing said sheath to bend away from opposite exterior curved edges on said primary and secondary handles;

holding said secondary handle stationary while pulling or pushing said primary handle upward or downward along an interior rail until a promixal end of said primary handle contacts a stop foot located at a proximal end of said secondary handle; and repeating said pulling and pushing actions several times to encourage plunging of said primary brush within said secondary brush, thereby promoting cells to be dislodged and released from said primary and secondary brushes, and transferred to said container of fixative solution.

* * * * *